United States Patent [19]
Zähner et al.

[11] 4,277,478
[45] Jul. 7, 1981

[54] ANTIBIOTIC AND USE THEREOF

[75] Inventors: Hans Zähner; Hannelore Drautz, both of Tübingen, Fed. Rep. of Germany; Walter Keller, Dübendorf, Switzerland

[73] Assignee: Ciba-Geigy Corporation, Ardsley, N.Y.

[21] Appl. No.: 41,279

[22] Filed: May 21, 1979

Related U.S. Application Data

[63] Continuation-in-part of Ser. No. 920,742, Jun. 26, 1978, abandoned, which is a continuation of Ser. No. 687,268, May 17, 1976, abandoned.

[30] Foreign Application Priority Data

| May 20, 1975 | [CH] | Switzerland | 6477/75 |
|---|---|---|---|
| Apr. 5, 1976 | [CH] | Switzerland | 4228/76 |
| May 15, 1976 | [DE] | Fed. Rep. of Germany | 2621690 |
| May 17, 1976 | [FR] | France | 76 14782 |
| May 17, 1976 | [IL] | Israel | 49591 |
| May 18, 1976 | [CA] | Canada | 252781 |
| May 18, 1976 | [CS] | Czechoslovakia | 3305/76 |
| May 18, 1976 | [GR] | Greece | 50739/205477 |
| May 18, 1976 | [HU] | Hungary | CI 1665 |
| May 18, 1976 | [NL] | Netherlands | 7605303 |
| May 18, 1976 | [ES] | Spain | 448024 |
| May 18, 1976 | [SU] | U.S.S.R. | 2357857 |
| May 19, 1976 | [AU] | Australia | 14080/76 |
| May 19, 1976 | [BE] | Belgium | 167140 |
| May 19, 1976 | [DK] | Denmark | 2214/76 |
| May 19, 1976 | [NZ] | New Zealand | 180898 |
| May 19, 1976 | [ZA] | South Africa | 76/2994 |
| May 19, 1976 | [GB] | United Kingdom | 20649/76 |
| May 20, 1976 | [JP] | Japan | 51-57357 |

[51] Int. Cl.³ ............... A61K 31/535; C07D 491/153
[52] U.S. Cl. .................................. 424/258; 546/37; 435/119
[58] Field of Search .................. 546/37; 424/258

*Primary Examiner*—Anton H. Sutto
*Assistant Examiner*—D. B. Springer
*Attorney, Agent, or Firm*—Prabodh I. Almaula

[57] ABSTRACT

The invention relates to the new antibiotic Lysolipin including two components X and I, and derivatives thereof. Lysolipin is formed when the strain *Streptomyces violaceoniger* (Waksman et Curtis) Waksman et Henrici Tü 96, which strain has been deposited under the reference NRRL 8097 at the Northern Regional Laboratory, U.S. Department of Agriculture, Peoria, Illinois, is cultured in a nutrient medium. The structural formulae of the 2 components are

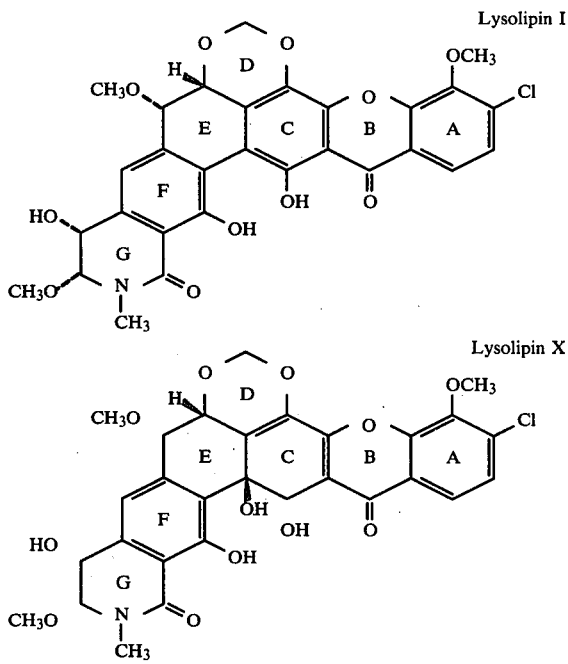

Lysolipin I and X and their derivatives have antibacterial activity and are effective against yeast - like fungi, such as *Candida albicans.* Their antibiotic action probably depends on an inhibition of the cell wall synthesis.

8 Claims, 8 Drawing Figures

Fig. 1

JR spectrum of Lysolipin I in KBr

Fig. 4

13C NMR spectrum of Lysolipin I in CDCl₃ and a little dimethylsulphoxide with complete noise decoupling

Fig. 6

100 MHz NMR spectrum of di-O-acetyl-Lysolipin I in CDCl₃

Fig. 7

100 MHz NMR spectrum of Lysolipin X in CDCl$_3$

ANTIBIOTIC AND USE THEREOF

This is a continuation-in-part of application Ser. No. 920,742 filed June 26, 1978, now abandoned, which is, in turn, a continuation application of Ser. No. 687,268 filed May 17, 1976, now abandoned.

The invention relates to the new antibiotic Lysolipin, which is insoluble in water and is present in the form of its components X and I or of mixtures of these components, and derivatives of the antibiotic and also formulations which contain these compounds and processes for the manufacture of these substances.

The antibiotic Lysolipin is formed when the strain Streptomyces violaceoniger (Waksman et Curtis) Waksman et Henrici Tü 96, which is kept under this reference in the Institute for Microbiology at the University of Tübingen (Germany), is cultured. The strain has been deposited under the reference NRRL 8097 at the Northern Regional Laboratory, U.S. Department of Agriculture, Peoria, Illinois.

The strain S. violaceoniger Tü 96 also forms a further antibiotic, namely Ropalocidin, which is described in the thesis by Dietmar Mahl "Ropalocidin ein antifungisches Antibiotikim aus Streptomyces violaceoniger" ("Ropalocidin, an anti-fungal antibiotic obtained from Streptomyces violaceoniger") Stuttgart, 1971.

The strain S. violaceoniger Tü 96 forms an aerial mycelium which is initially white and later ash-grey. The spore chains are monopodially branched and in the shape of tight regular spirals which seldom comprise more than three turns. The spores are ellipsoidal, about 0.9 nm wide and 1.2 nm long and have a smooth surface. No melanoid discoloration is observed when the strain is grown on peptone-containing culture media (peptone-iron agar), even after incubating for several days. Thus, the strain displays no chromogenesis since it is not able to form any tyrosinase.

The antibiotic Lysolipin is obtained by culturing the strain S. violaceoniger Tü 96, or a mutant of this strain which forms Lysolipin, under aerobic conditions in an aqueous nutrient solution, which contains a source of carbon and a source of nitrogen as well as inorganic salts, until the nutrient solution displays a considerable antibiotic action, and then isolating the antibiotic Lysolipin from the culture filtrate. Mutants which form the antibiotic can be obtained, for example, under the action of ultraviolet rays or X-rays or of nitrogen-mustards.

Examples of sources of carbon which may be mentioned are: assimilable carbohydrates, for example glucose, sucrose, lactose, mannitol, starch and glycerol. Nitrogen-containing nutrient substances which may be mentioned are: aminoacids, peptides and proteins as well as their degradation products, such as peptone or tryptone, and also meat extracts and watersoluble constituents of cereal grains, such as maize and wheat, of distillation residues from the manufacture of alcohol, of yeast, beans, especially of the soya bean plant, and of seeds, for example of the cotton plant, and the like, but also ammonium salts and nitrates. Amongst other inorganic salts, the nutrient solution can contain, for example, chlorides, carbonates, sulphates and phosphates of alkali metals or alkaline earth metals or of magnesium, iron, zinc and manganese.

The culture is carried out aerobically, that is to say, for example, in a stationary surface culture or, preferably, as a submersed culture, the culture being shaken or stirred with air or oxygen in shaking flasks or the known fermenters. A suitable temperature is between 18° and 40° C., preferably 27° C. In general, the nutrient solution then displays a substantial antibiotic action after 3 to 7 days. Preferably, the cultivation is carried out in several stages, that is to say one or more preliminary cultures are first prepared in a liquid nutrient medium and are then inoculated, for example in a ratio of 1:20, into the actual production medium. The preliminary culture is obtained, for example, by inoculating a mycelium which has formed spores and has been obtained by growing for about 14 days on a culture medium, into a liquid medium and allowing it to grow for 72 hours.

the antibiotic is contained in the culture filtrate. The antibiotic is isolated from the culture filtrate by methods which are in themselves known, taking into account the chemical, physical and biological properties, and especially the lipophilic properties, of the antibiotic. Bacillus subtilis is particularly suitable as a test organism for testing the antibiotic action (that is to say the presence of the antibiotic).

The antibiotic can be extracted from the culture filtrate using a lipophilic solvent which is immiscible with water, for example using ethyl acetate or hydrocarbons, such as cyclohexane or benzene, or using halogenated hydrocarbons, for example methylene chloride, chloroform, carbon tetrachloride or tetrachloroethylene.

Methods which can be used to purify the crude product obtained after evaporating off the solvent are, for example, extraction, precipitation, partition between immiscible solvent phases or adsorption, and above all chromatography. A large proportion of the more lipophilic impurities can be removed by extracting the crude product with petroleum ether. It is also possible to dissolve the crude product, for example in methanol, and to separate off impurities by means of adsorbents, such as active charcoal, silica gel, magnesium silicate, aluminium oxide or mixtures thereof or by means of adsorption resins, for example crosslinked dextrans, such as "Sephadex" (from Messrs. Pharmacia Fine Chemicals, Uppsala). For example, the crude product can be purified by repeated column chromatography using silica gel, appropriately with small additions of active charcoal. The antibiotic is preferably eluted by the gradient method with mixtures of chloroform or carbon tetrachloride and methanol, the percentage content of the more strongly polar solvent being increased stepwise.

The abovementioned partition between immiscible solvent phases can also be carried out as a counter-current partition using a Craig apparatus. The solvent system used is, for example, a mixture of chloroform, cyclohexane, methanol and water.

In order to obtain the individual single components of the antibiotic, these can be separated and isolated, for example, by the method of preparative thin layer chromatography under the conditions described for the analytical identification. Separation by means of column chromatography, in which, for example, silica gel containing 1–5 percent of active charcoal is used as the adsorbent and the elution is preferably effected by the gradient method using a mixture of chloroform and methanol, is more advantageous. The concentration of the less polar solvent is appropriately increased in relatively small percentage steps, for example 5–20% of chloroform, or the continuous gradient elution method is used. The purification process can be repeated if necessary.

The components display the following Rf values in a thin layer chromatogram on silica gel plates from Messrs. Merck (silica gel 60, F254): in chloroform/methanol (9:1): X=0.58; I=0.81; in benzene/methanol (9:1): X=0.26; I=0.30; in chloroform/acetone (5:5): X=0.40; I=0.53; and in benzene/acetone (5:5): X=0.47; I=0.74. In a serial dilution test the following minimum inhibitory concentrations (MIC) were found for Lysolipin I:

| Micro-organisms | MIC in γ/ml Lysolipin I | |
| --- | --- | --- |
| Eubacteriales (Gram-negative) | | |
| *Achromobacter geminiani* (27°) | >0.0025 | <0.005 |
| *Salmonella minnesota* (37°) | >0.5 | <1 |
| *Salmonella typhimurium* (37°) | >100 | |
| *Proteus vulgaris* (37°) | >0.001 | <0.0025 |
| Eubacteriales (Gram-positive) | | |
| *Arthrobacter aurescens* (27°) | >0.001 | <0.0025 |
| *Arthrobacter crystallopoietes* (27°) | >0.001 | <0.0025 |
| *Arthrobacter simplex* (27°) | >0.001 | <0.0025 |
| *Bacillus brevis* (37°) | >0.025 | <0.05 |
| *Bacillus megaterium* (37°) | >0.001 | <0.0025 |
| *Bacillus subtilis* (37°) | >0.001 | <0.0025 |
| *Brevibacterium flavum* (27°) | >0.001 | <0.0025 |
| *Clostridium pasteurianum* (30°) | >0.001 | <0.0025 |
| *Chromobacterium violaceum* (27°) | >0.1 | <0.5 |
| *Corynebacterium poinsettiae* (27°) | >0.001 | <0.0025 |
| *Corynebacterium rathayi* (27°) | >0.001 | <0.0025 |
| *Micrococcus luteus* (27°) | >0.001 | <0.0025 |
| *Micrococcus roseus* (27°) | >0.001 | <0.0025 |
| *Sarcina lutea* (27°) | >0.001 | <0.0025 |
| *Staphylococcus aureus* (37°) | >0.001 | <0.0025 |
| Pseudomonadales | | |
| *Pseudomonas fluorescens* (27°) | >0.001 | <0.0025 |
| *Pseudomonas saccharophila* (27°) | >0.001 | <0.0025 |

For Lysolipin X the MIC is higher by a factor of 10–50. Lysolipin I has the following chemical and physical properties:

It is a deep yellow crystalline substance which is virtually insoluble in water and aqueous acids and bases; it is partially soluble in lower alkanols, such as methanol, ethanol and n-propanol, and also in ether and petroleum ether. It is readily soluble in acetone, dimethylformamide, dimethylsulphoxide, ethyl acetate, hydrocarbons, for example cyclohexane and benzene, and halogenated hydrocarbons such as those mentioned above.

When crystallised from acetone/ether, Lysolipin I melts at 260°–262° with decomposition. $[\alpha]_D^{20} = -50.2°$ (chloroform). On thin layer chromatography on silica gel in the system chloroform/methanol (19:1), Rf=0.6.

Elementary analysis gives the following values:

$C_{29}H_{24}ClNO_{11}$ (597.95): Calculated: C 58.25, H 4.05, Cl 5.93, N 2.34, 3 $OCH_3$, 15.57%: Found C 58.36, H 4.22, Cl 6.03, N 2.48, $OCH_3$ 15.43%: C 58.30, H 4.27, N 2.38.

($OCH_3$: determination according to the method of Zeisel). Molecular weight, determined by vapour pressure osmometry in ethyl acetate; found 536. Microtitration with 0.1 N tetramethylammonium hydroxide in methylcellosolve/water (8:2): found $pK^x_{MCS}$ 9.72, equivalent weight 545. Titration with 0.1 N HCl; no step (N atom therefore not basic).

Figure 1:
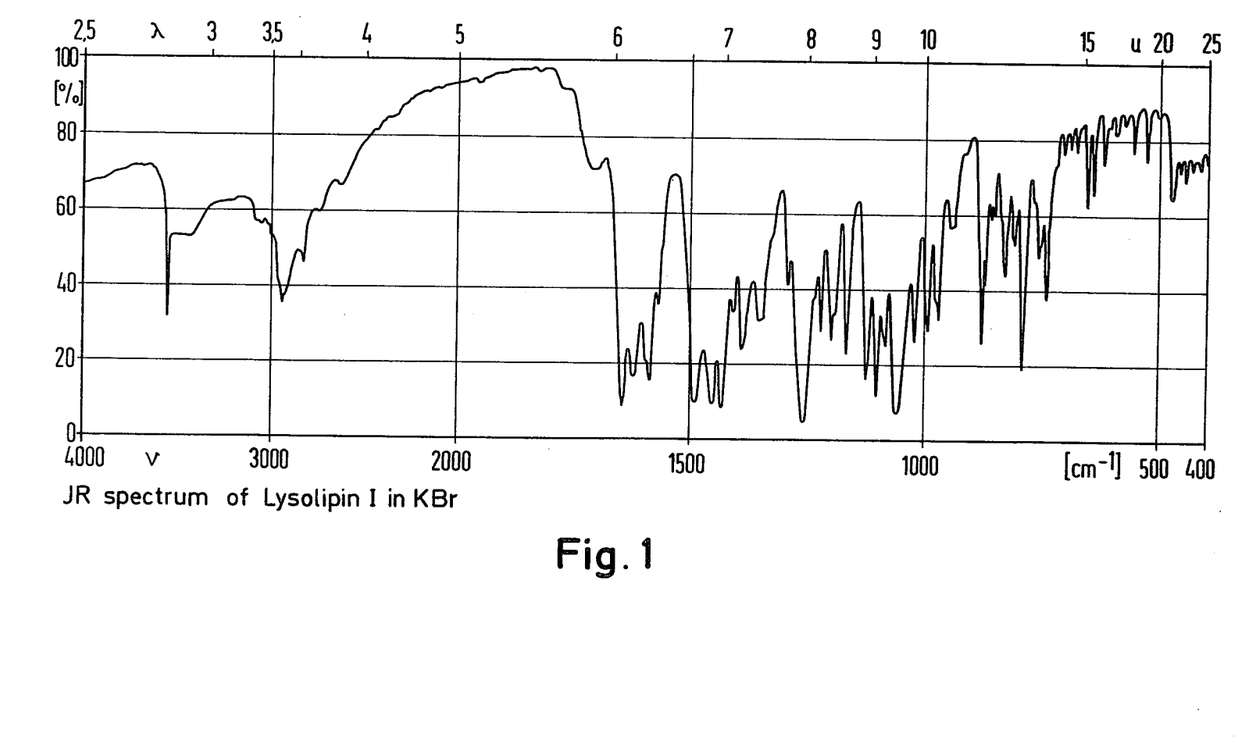
FIG. 1: IR spectrum of Lysolipin I in KBr.
Figure 2:
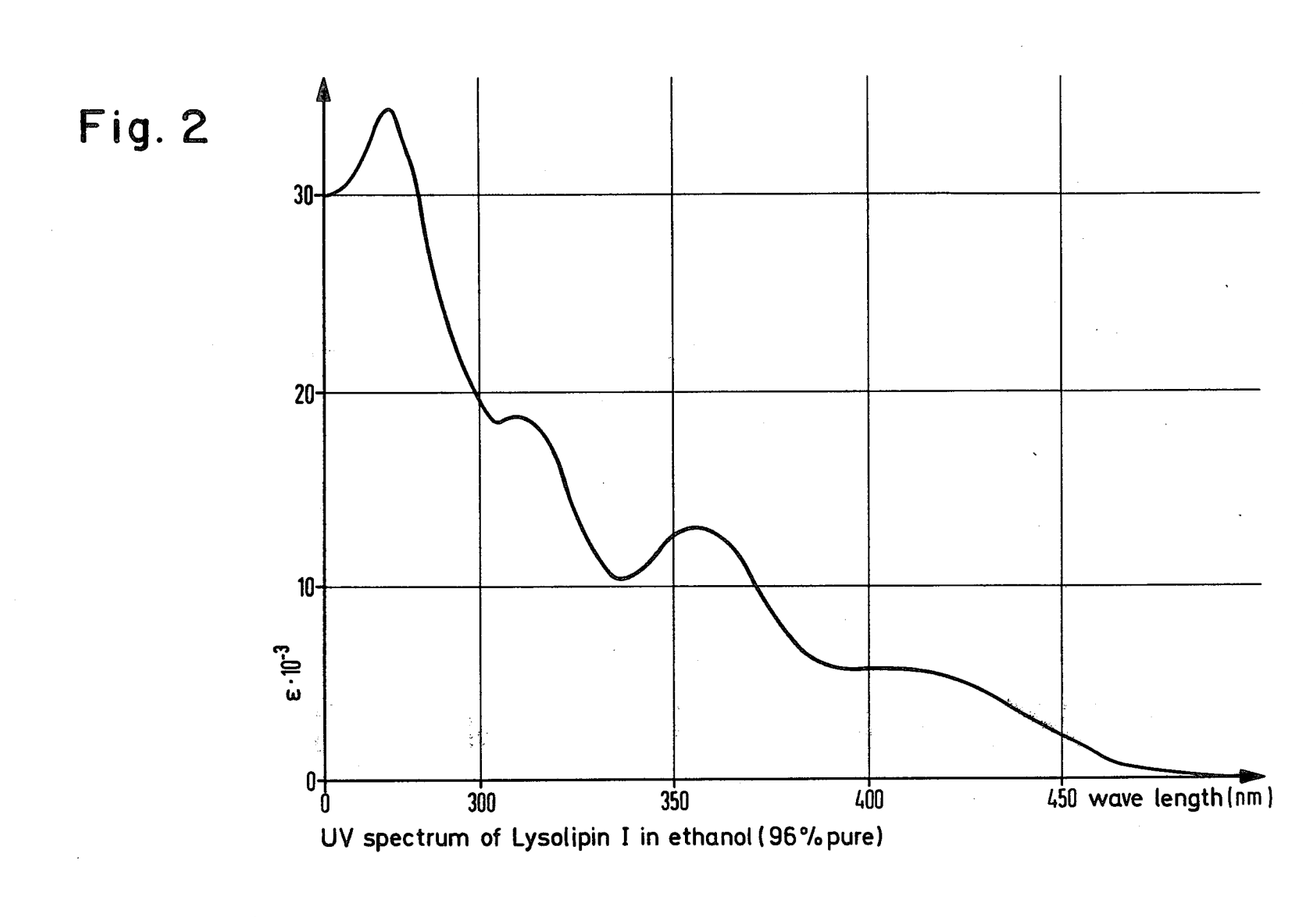
FIG. 2: UV spectrum of Lysolipin I in rectified spirit.
Figure 3:
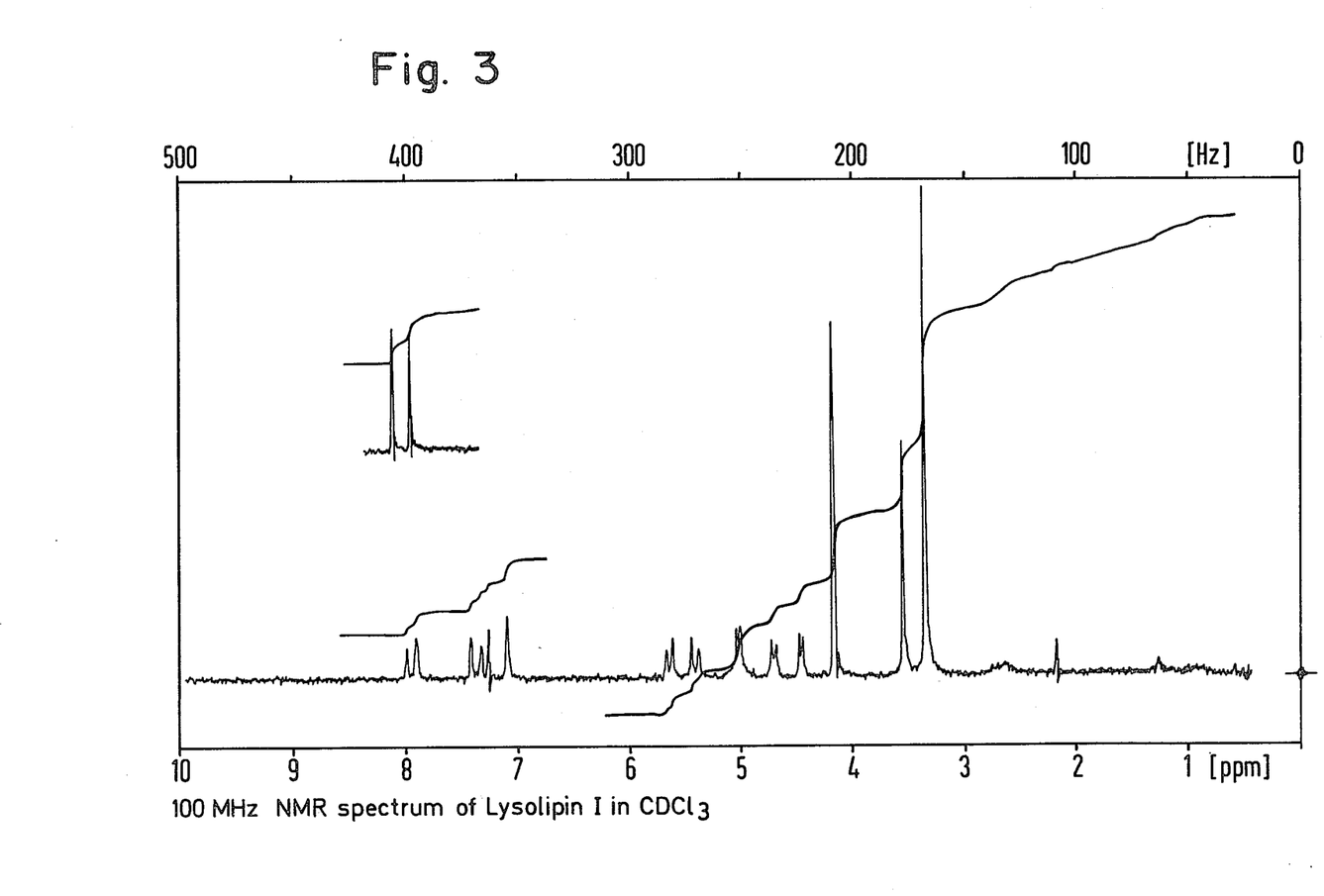
FIG. 3: NMR spectrum of Lysolipin I in CDCl$_3$.
Figure 4:
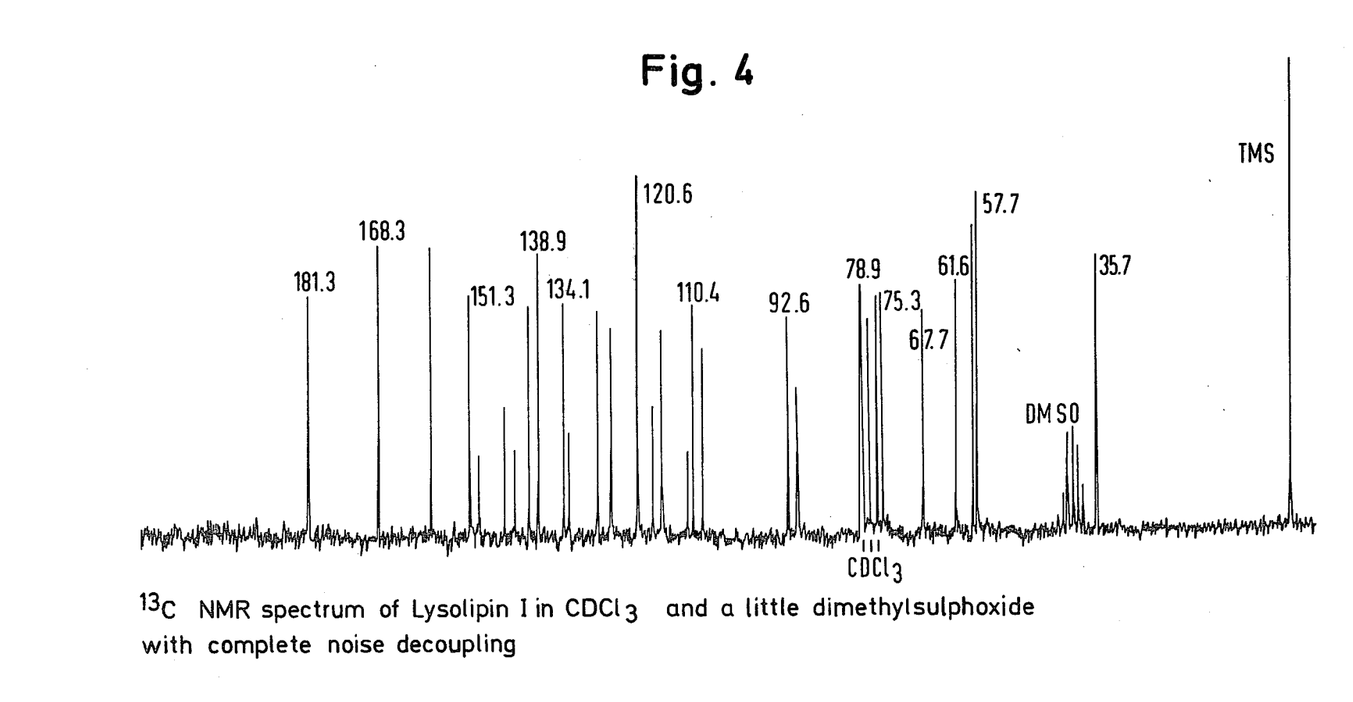
FIG. 4: $^{13}$C NMR spectrum of Lysolipin I with complete noise decoupling.
Figure 5:
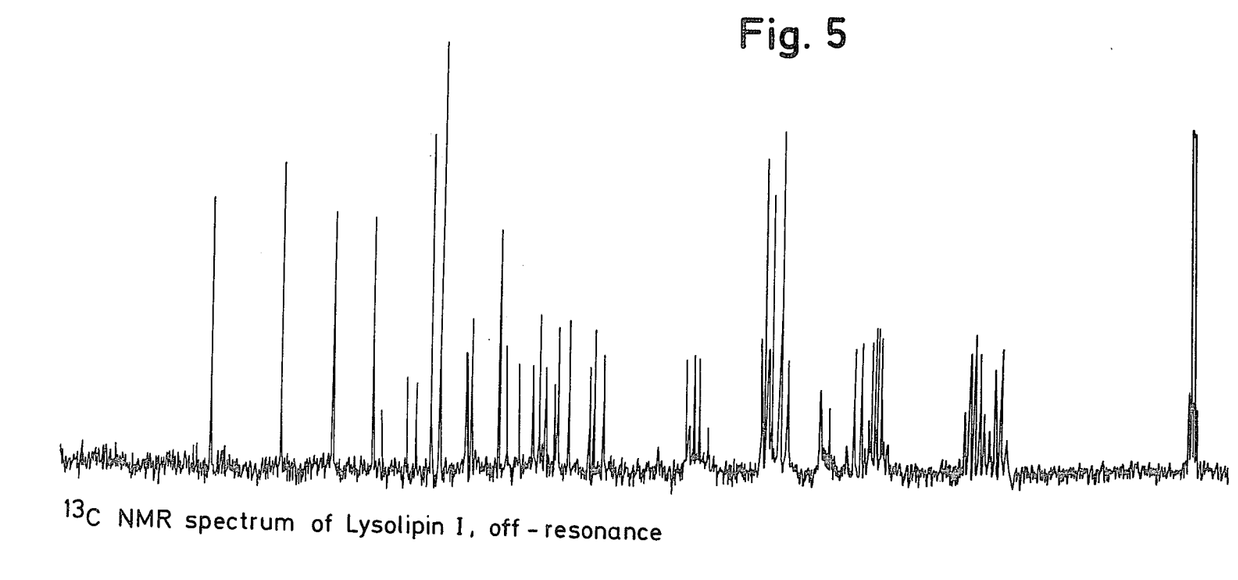
FIG. 5: $^{13}$C NMR spectrum of Lysolipin I, off-resonance.

FIG. 1 shows the IR spectrum of Lysolipin I in KBr and FIG. 2 shows the UV spectrum in ethanol (96% pure). FIG. 3 shows the NMR spectrum in $CDCl_3$ (100 MHz); only the two signals in the offset region and the broad signal at about 2.7 ppm disappear on exchange with $D_2O$. FIG. 4 shows the $^{13}C$ NMR spectrum in $CDCl_3$ and a little dimethylsulphoxide with complete noise decoupling and FIG. 5 shows the off-resonance $^{13}C$ NMR spectrum. Table 1 gives a compilation of the maxima from FIG. 4. Table 2 shows the mass spectrum of Lysolipin I.

The following supplementary statements are to be made in respect of the NMR spectrum (FIG. 3):

(1.) Spin decoupling.

Incident radiation at 4.43: the doublet at 5.02 ppm becomes a singlet. Incident radiation at 5.02 ppm: the doublets at 4.43 and 4.68 ppm simultaneously become singlets.

When integrated, the signal at 5.02 ppm corresponds to 2 protons and can be regarded as a superposition of a doublet and a broad multiplet. The doublet is interdependent on that at 4.43 ppm and the multiplet is interdependent on the doublet at 4.68 ppm.

(2.) The precise coupling constants were measured on a spectrum extended to four times the length and gave: 4.43 (d): 3.0 Hz., 4.68 (d): 4.1 Hz., 5.02 (d): 3.0 Hz., 5.40 (d): 5.7 Hz. and 5.62 (d): 5.7 Hz. The last two signals together form a AB spectrum, as do the two doublets at 7.36 and 7.90 ppm ($J_{AB}=8$ Hz., hydrogen atoms in the o-position in an aromatic ring).

Figure 6:
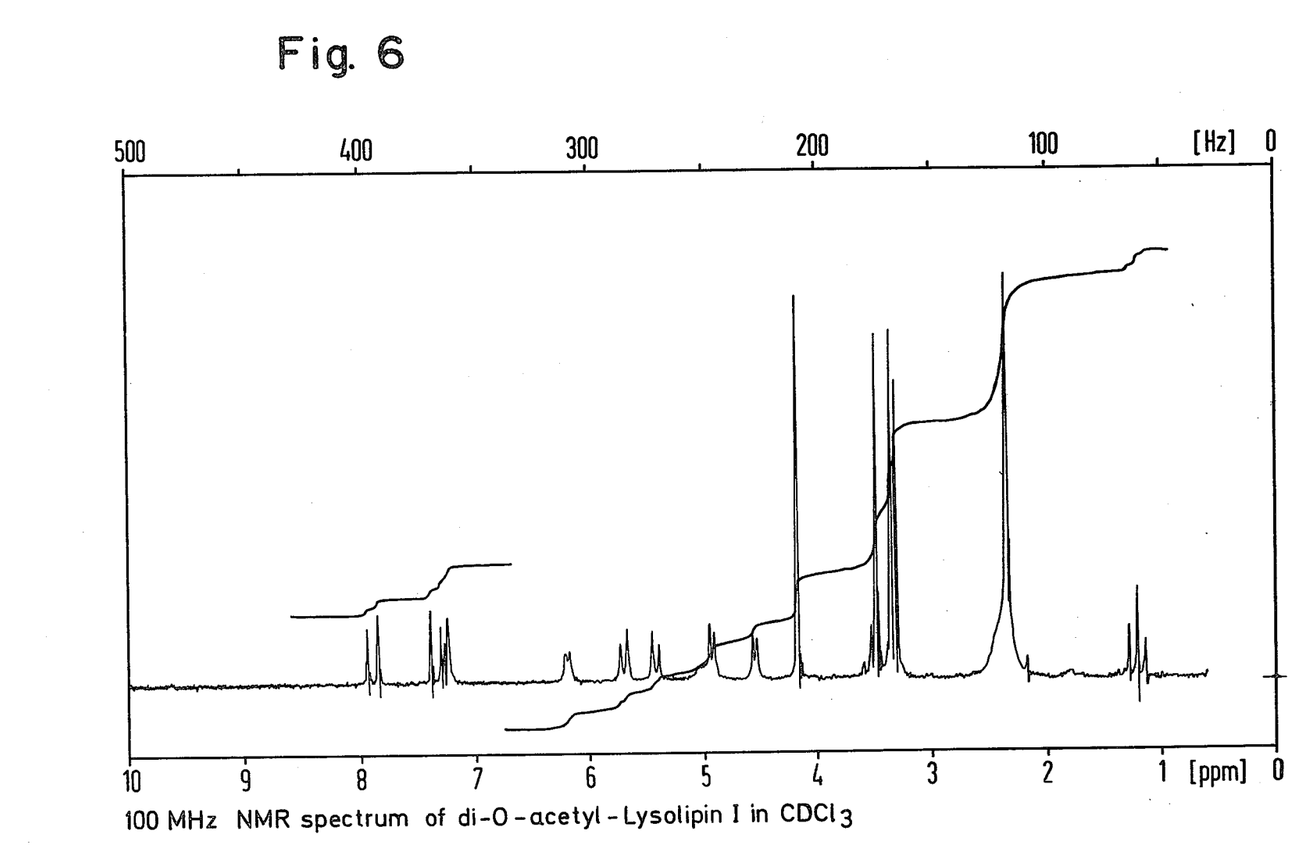
FIG. 6: NMR spectrum of tri-O-acetyl-Lysolipin I in CDCl$_3$

Lysolipin I contains two hydroxyl groups which can be easily acylated. Prolonged acetylation (2 weeks at room temperature) gives tri-O-acetyl-Lysolipin I, which was crystallised from acetone/water; pale yellow crystal prisms with a melting point of 216°–224°. FIG. 6 shows the NMR spectrum in $CDCl_3$ (100 MHz). The sample of the substance which was used still contained ethyl acetate. This causes the following signals: the triplet at 1.2 ppm; a quartet, which is partially overlapped by $OCH_3$ signals, at about 3.5 ppm and a proportion of the signal at about 2.35 ppm. Table 3 gives the mass spectrum of tri-O-acetyl-Lysolipin I.

When the acylation is carried out only overnight, as is customary, a mixture of two products which cannot be separated by crystallisation is obtained; these products are apparently a monoacetate and a diacetate. The monoacylates of Lysolipin I, in particular the monoacetate, can be obtained by acylating during a short period of time, for instance 2–4 hours.

A separation of monoacetate, diacetate and triacetate in mixtures obtained by acetylation of Lysolipin of varying duration can be achieved by other standard purification procedures, such as chromatography, e.g. on silicagel or aluminum oxide or adsorption on resins, such as cross-linked dextrans, e.g., "Sephadex", especially "Sephadex LH-20" or "Amberlite XAD"—resins, or by distribution between non miscible solvents.

By using other acylating agents, such as for instance those derived from other carboxylic acids, for instance other lower carboxylic acids of the aliphatic series having from 1 to 7 C-atoms, the corresponding monoacyl-, diacyl- and triacyl- derivatives can be obtained in an analogous manner, and they can be separated in much the same manner as described above for the acetates.

The following structural formula was determined for component I of Lysolipin by X-ray spectrometry:

C29H24ClNO11
Lysolipin I

Lysolipin X was obtained as a colourless amorphous powder. It forms Lysolipin I on heating or on irradiation with UV light, especially in the presence of catalytic amounts of acids. It can, however, also be converted into Lysolipin I by being treated in a suitable solvent, e.g. chloroform or methanol, with an acid, e.g. a carboxylic acid, such as a lower aliphatic carboxylic acid, e.g. formic or acetic acid, or an inorganic acid such as hydrochloric or sulfuric acid, into Lysolipin I. It is unstable when impure; when stored in the air, and unprotected from light, especially at room temperature or at a higher temperature, it is gradually converted into Lysolipin I. It was possible to achieve a partial separation of Lysolipin X and I by Craig distribution in the system carbon tetrachloride/chloroform/methanol/water (3.42:2.28:4:1). The almost colourless amorphous powder thus obtained, that is to say Lysolipin X, can be crystallized from methanol; on heating the crystals undergo modification at 200° and melt at 260° C.

Figure 7:
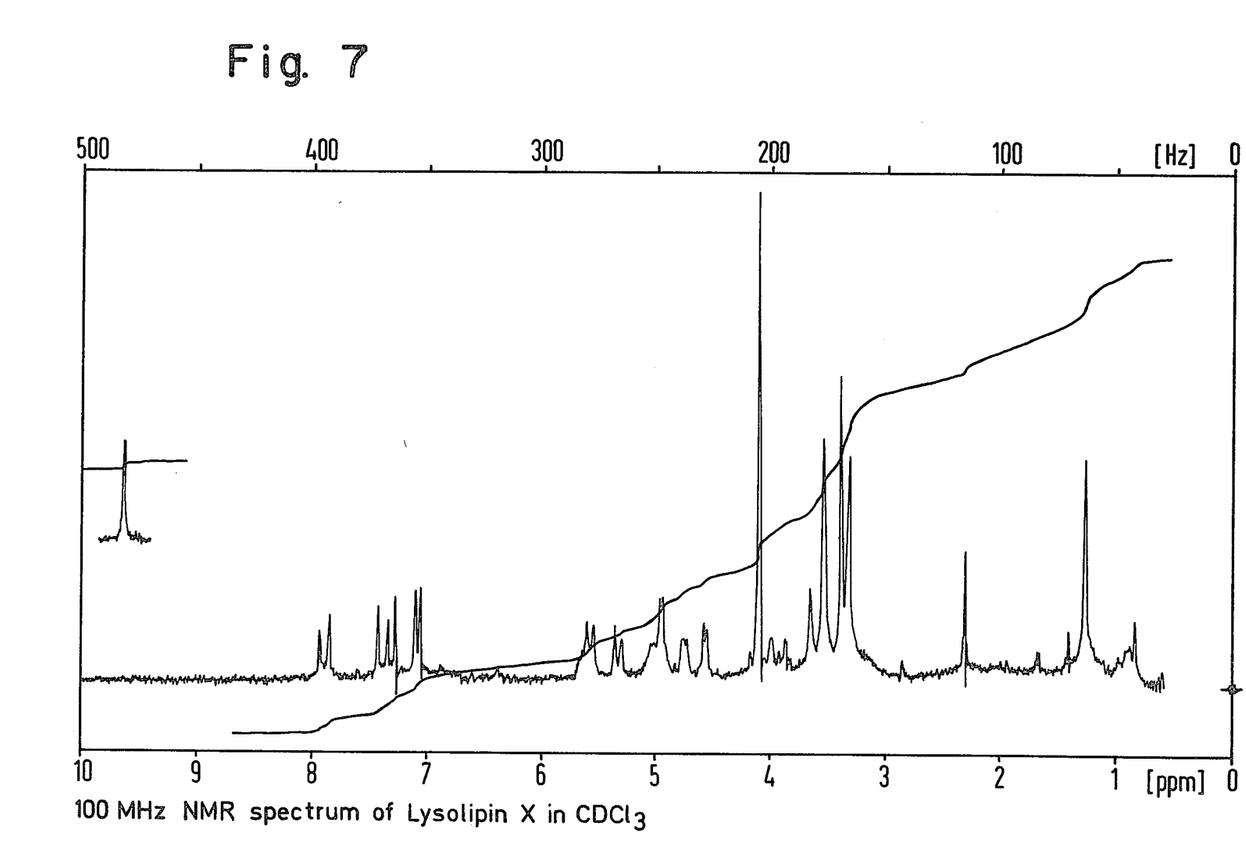
FIG. 7: NMR spectrum of Lysolipin X which was not completely pure (in CDCl$_3$ 100 MHz).
Figure 8:
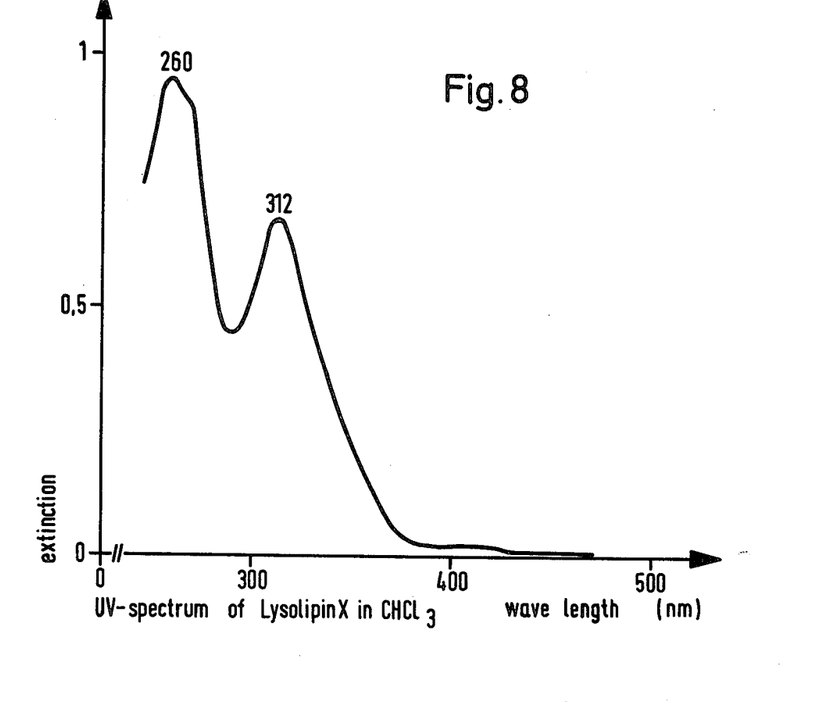
FIG. 8: UV spectrum of Lysolipin X in CHCl$_3$.

The compound possesses the optical rotation $[\alpha]_D^{20} = -349° \pm 1°$ (c=1,19 in CHCl$_3$). The pure product so obtained is stable in the absence of light and acid. In a thin layer chromatogram on silica gel in the system chloroform/methanol (39:1), Rf=0.22 (Rf of Lysolipin I=0.39). FIG. 7 shows the 100-MHz-NMR spectrum of Lysolipin X in CDCl$_3$. The signals at 0.9 and 1.3 ppm are probably to be ascribed to a fatty impurity. However, most of the signals in the range from 3 to 8 ppm are very similar to those of Lysolipin I and point to the close relationship between the two compounds. FIG. 8 shows the UV spectrum of Lysolipin X in chloroform.

The mass spectrum of Lysolipin X shows signals m/e at 597 (M$_1$-H$_2$O, 1Cl), 567, 565, 536, 519, 504, 328 and 233. On the basis of these data, the $^{13}$C-NMR-spectrum (reported in Table 4) and the X-rays analysis the following structural formula could be established for Lysolipin X C29H26ClNO12

The X ray analysis has also shown that in the crystalline state Lysolipin X includes also one half mole of water per one mole of the above formula.

The Infrared absorption (IR) spectrum for Lysolipin X is given in Table 5.

When Lysolipin X is acylated, for instance acetylated, for a short period of a few hours, e.g. 2-4 hours, at room temperature, a Lysolipin X monoacylate, in particular a monoacetate, is obtained. A suitable method for the manufacture of Lysolipin X monoacetate is for instance described in Example 6. There can be prepared in an analogous manner monoacyl derivatives of other lower aliphatic carboxylic acids, for instance those having from 1 to 7 C atoms.

On prolonged acylation of Lysolipin X, for instance during about 12 hours, a mixture of diacylates and the monoacylates, such as the diacetate and the monoacetate, or the esters of the other acids mentioned above, can be obtained. They can be isolated individually by the methods of purification described above for the esters of Lysolipin I. On exhaustive acylation, for instance over a period of 3 to 5 days, the triacylates, e.g. the triacetate can be obtained.

In addition to their antibacterial action against bacteria, Lysolipin, both in the form as obtained by fermentation as a mixture of its 2 components, Lysolipin I and Lysolipin X, and in the form of each of these components, and its derivatives also display an activity against yeast-like fungi, such as *Candida albicans, Candida lipolytica* and *Saccaromyces cerevisiae*. They are active against both growing and dormant microbial cells and also against their sphaeroplasts. Its action probably depends on an inhibition of the cell wall synthesis. The action is partially cancelled by an excess of lipids, for example sphingolipids, phosphoglycerides and bacterial cell wall lipids.

Lysolipin and its derivatives can be used, on their own or in combination with other antibiotics which inhibit the cell wall synthesis, such as penicillins, cephalosporins and cycloserine, to combat infections, which are caused by bacteria such as those mentioned, and as disinfectants.

In order to manufacture pharmaceutical formulations, the antibiotic can be mixed with an inorganic or organic excipient which is suitable for topical application or for enteral or parenteral administration. Excipients which can be used are those substances which do not react with the new compound, such as, for example, gelatine, lactose, starch, magnesium stearate, vegetable oils, benzyl alcohols or other medicinal excipients. The pharmaceutical formulations can be in the form of, for example, tablets, dragees, powders or suppositories or in a liquid form as solutions, suspensions, emulsions, creams or ointments. Optionally, the formulations are sterilised and/or contain auxiliaries, such as preservatives, stabilisers, wetting agents or emulsifiers. They can also contain further therapeutically valuable substances. The disinfectants can also be mixed with suitable excipients, as is known.

The invention is described in the examples which follow. The temperatures are quoted in degrees Centigrade.

The Figures show.

The Tables show:

Table 1: mass spectrum of Lysolipin I.
Table 2: $^{13}$C NMR spectrum of Lysolipin I.
Table 3: mass spectrum of tri-O-acetyl-Lysolipin I.
Table 4: $^{13}$C-NMR spectrum of Lysolipin X.
Table 5: IR-spectrum of Lysolipin X.

EXAMPLE 1

A lyo-ampoule containing 5 ml of a suspension of the spores of S. violaceoniger Tü 96 is suspended with 5 ml of a 0.2 M phosphate buffer which has a pH of 7. 3 conical flasks which have 1 breaker (identification, "baffle") and which each contain 100 ml of a nutrient solution which contains 4 g of yeast extract, 10 g of malt extract and 4 g of glucose per liter of tapwater and the pH of which has been adjusted, prior to sterilisation, to 7.3 with 1 N sodium hydroxide solution, are each inoculated with 2 ml of the Streptomyces suspension and incubated for 24 hours at 27° on a shaking machine which is rotating at 250 rpm. 25 ml portions of the culture thus obtained are inoculated into six 2 liter conical flasks which have 4 baffles and 500 ml of the above nutrient solution. The flasks are then incubated at 27° for 48 hours on a shaking machine which is rotating at 120 rpm.

0.75 liter of the culture from the 2 liter flasks is transferred into a 50 liter fermenter, which contains 30 liters of the above nutrient solution, and incubated for 24 hours at 27°. 15 liters of the culture are then transferred into a fermenter which contains 300 liters of the above nutrient solution. This fermenter has a total volume of 500 liters and contains a 6-bladed turbine stirrer and 4 baffle plates (deflector "baffles"). The culture conditions in the fermenter are: pressure 0.5 atmospheres gauge, stirring speed 450 rpm, temperature 27° C. and air throughput 1 liter V/V.minute. The conditions correspond to a rate of oxygen absorption, measured in sulphite solution, of 150 mmols O$_2$/liter/hour. Optimum formation of the antibiotic Lysolipin takes place after about 100 hours incubation. The culture solution then has a pH of 7.5. In an agar diffusion test with *Bacillus subtilis* the culture solution produces an inhibition zone of 14–15 mm diameter when Whatmann A filter discs of 6 mm are used.

EXAMPLE 2

600 liters of the culture solution obtained according to Example 1 are filtered, 2% of "Dicalite" filter auxiliary (diatomaceous earth) being added. 560 liters of the culture filtrate are adjusted to a pH of 9.0 with sodium hydroxide solution and extracted twice, in a continuous extractor, with chloroform in a ratio of 2:1. The inactive aqueous raffinate is discarded. 600 liters of the chloroform phase are concentrated in vacuo. 290 g of a dry residue result. This residue is digested with 2 liters of petroleum ether. The inactive petroleum ether extract is discarded and the insoluble fraction is dried in vacuo. A yellow-brown semi-solid residue (46 g) remains.

EXAMPLE 3

2.8 g of the crude product obtained according to Example 2 are chromatographed in a column of Sephadex ® LH-20 (alkylated, crosslinked dextran), which has a length of 73 cm and a diameter of 3 cm, with chloroform/methanol (1:1) at a rate of 20 ml per hour. 5 ml fractions are collected. The relative content of Lysolipin I in the fractions is determined photometrically at 360 nm; the content of Lysolipin I determined in fractions 40–47 is arbitrarily taken as 1. The following distribution results:

| Fraction | mg of dry residue | relative content of Lysolipin I |
| --- | --- | --- |
| 1–27 | 40 | below 0.05 |
| 28–29 | 30 | 0.46 |
| 30–39 | 524 | 0.58 |
| 40–47 | 618 | 1 |
| 48–55 | 234 | 0.29 |
| 57–80 | 233 | below 0.1 |

From acetone/ether, fractions 40–47 give 416 mg of deep yellow crystals of Lysolipin I with a melting point of 260°–262° (decomposition). Further chemical, physical and biological properties are listed in the general section of the description.

A further 360 mg of crystals can be obtained from the mother liquors from the crystallisation and from the adjacent fractions by chromatographing again on Sephadex ® LH-20.

EXAMPLE 4

300 mg of Lysolipin I are left to stand with 10 ml of pyridine and 10 ml of acetic anhydride for 2 weeks at room temperature and the solution is then evaporated in vacuo. The residue is chromatographed on 30 g of silica gel with chloroform/ethyl acetate (4:1). The first 150 ml of eluate contain 48 mg of inhomogeneous material. The next 210 ml give 220 mg of a pale yellow oily material which, in a thin layer chromatogram (silica gel, with ethyl acetate as the flow agent; staining with iodine vapour), shows a main spot with a Rf of 0.33 and two faint impurities. Pale yellow crystal prisms which have an indefinite melting point of 216°–224° form on slow crystallisation from acetone/water. See FIG. 6 for the NMR spectrum in CDCl$_3$ (100 MHz). The sample still contains some ethyl acetate (from the chromatography), which becomes apparent in the NMR spectrum. On the basis of the mass spectrum (see Table 3), the compound is a triacetate.

When the acetylation is carried out only overnight, as is customary, a mixture of two products which cannot be separated by crystallisation is obtained; these products are apparently a monoacetate and the diacetate. In the mass spectrum of this mixture the signals at 683 and 681 mass units (M+ of the diacetate) occur with a substantially lower intensity.

EXAMPLE 5

1.5 g of the crude product obtained according to Example 2 are subjected to a Craig distribution over 190 steps in the solvent system carbon tetrachloride (3.42 liters)/chloroform (2.28 liters)/methanol (4 liters)/water (1 liter). The deep yellow coloured fractions 26–54 contain mainly Lysolipin I. This is isolated by diluting the fractions with twice the volume of water, separating off the organic phase, extracting the aqueous phase by shaking three times with methylene chloride and combining the organic phases, drying them with sodium sulphate and evaporating in vacuo. 258 mg of Lysolipin I, which according to thin layer chromatography is a single product, are obtained and are further purified by chromatography on Sephadex ® LH-20 and recrystallisation, as described above.

On analogous working up, fractions 76–100 give an almost colourless amorphous powder (393 mg), which is Lysolipin X and cannot be purified by crystallisation. See FIGS. 7 and 8 for the NMR spectrum and the UV spectrum. On thin layer chromatography on silica gel in chloroform/methanol (39:1), Rf=0.22 (compared with 0.39 for Lysolipin I). On the thin layer plate, the spot for Lysolipin X, which is initially very pale and scarcely discernible, becomes deep yellow on standing in the air and, more rapidly, on warming. When the spot is eluted and thin layer chromatography is carried out again it is found that Lysolipin X has been converted into Lysolipin I.

EXAMPLE 6

0.240 g of Lysolipin X are added to a solution of 2.48 g of tetra-(n-butyl)-ammoniumfluoride-trihydrate, which has been dried for 48 hours in a high vacuum, in 30 ml of methylene chloride. A solution of 1.88 ml of acetic anhydride in 10 ml of methylene chloride ist then dropped in over a period of 15 minutes. At the end of the addition only traces of the starting material can be detected on thin-layer chromatographic analysis. After a reaction time of two hours at room temperature the reaction mixture is poured on ice water and the reaction product is extracted three times with chloroform. The yellow residue which is obtained on evaporation is chromatographed on about 100 g of "Sephadex LH-20" resin. Lysolipin X monoacetate is obtained by elution with methanol as a beige colored substance. A small amount of yellow crystals are eluted from further fractions, which are identical with Lysolipin I monoacetate when compared with an authentic sample prepared in the same manner as above starting from Lysolipin I.

EXAMPLE 7

0.70 g of Lysolipin X are dissolved in 35 ml of chloroform-methanol mixture 1:1 and 0.1 ml of formic acid is added. The slightly yellow colored solution is refluxed for 30 minutes at a bath temperature of 105°. No starting material can be detected after this time by thin-layer chromatography. The chloroform is evaporated off on a rotating evaporator from the brown-reddish reaction solution and the methanolic concentrate so obtained is stored in a refrigerator overnight, whereupon Lysolipin I crystallizes in the form of golden colored needles. 0.57 g crystallisate is obtained by filtration and drying. On evaporation of the mother liquor 0.115 g of semi-crystalline residue is obtained, which consists of contaminated Lysolipin I. The first pure fraction is recrystallized again from about 15 ml of methanol and dried for 48 hours at 35° in a high vacuum. The product obtained melts at 260°–262°.

EXAMPLE 8

100 ml of a spore suspension of Streptomyces violaceoniger NRRL 8097 (Tü 96) in a 0.2 M pH 7.0 phosphate buffer containing $10^6$ spores/ml is inoculated directly into a 500 l fermenter containing 300 l of a nutrient medium consisting of 4 g of yeast extract, 10 g of malt extract and 4 g of glucose per liter of tap water. The pH of the medium is adjusted to 7.3 with 1 N sodium hydroxide prior to sterilization. The fermenter is equipped with one 6-bladed turbine stirrer of 230 mm diameter and which has no baffles. The culture condition in the fermenter are: pressure 0.5 bar, stirring speed 350 r.p.m., temperature 27° C., air-through put 1 liter/v/v minute. Optimum formation of the antibiotic Lysolipin is after 120–144 hours fermentation time. The culture broth then has a pH of 7.8. In an agar diffusion test with Bacillus subtilis on a synthetic agar medium the undiluted whole broth gives an inhibition zone of 14–15 mm diameter with Whatmann A filter discs of 6 mm.

Lysolipin is isolated from the fermentation broth in the form of its two components Lysolipin I and Lysolipin X in the manner described in Example 5.

TABLE 1

Lysolipin I.
$^{13}$C NMR spectrum (25.2 MHZ). Solvent: $CDCl_3$ + a little DMSO

| No. | δ(ppm) | m | | No. | δ(ppm) | m |
|---|---|---|---|---|---|---|
| 1. | 181.26 | s | | 13. | 125.48 | d |
| 2. | 168.26 | s | | 14. | 120.62 | ? |
| 3. | 158.60 | s | | 15. | 117.77 | s |
| 4. | 151.26 | s | | 16. | 116.15 | d |
| 5. | 149.65 | s | | 17. | 111.24 | s |
| 6. | 144.95 | s | | 18. | 110.37 | s |
| 7. | 143.17 | s | | 19. | 108.54 | s |
| 8. | 140.53 | s | | 20. | 92.63 | d |
| 9. | 138.86 | s | | 21. | 90.95 | t |
| 10. | 134.06 | s | | 22. | 78.87 | d |
| 11. | 133.09 | s | | 23. | 75.31 | d |
| 12. | 127.91 | s | | 24. | 67.70 | d |
| 25. | 61.55 | q | $OCH_3$ | 27. | 57.67 | q | $OCH_3$ |
| 26. | 58.42 | q | $OCH_3$ | 28. | 35.55 | q | |

δ: Chemical shift relative to tetramethylsilane as the internal standard. m: resolution in the "off resonance" spectrum. 28 of the 29 C atoms are discernible as independent signals.

TABLE 2

Lysolipin I
Yellow crystals, $C_{29}H_{24}ClNO_{11}$
Mass spectrum. Di = 140° C.

| m/e | % | m/e | % | m/e | % |
|---|---|---|---|---|---|
| 601 | 0.2 | 566 | 1.0 | 524 | 0.3 |
| 600 | 1.0 | 565 | 2.2 | 523 | 0.2 |
| 599 | 3.2 | | | 522 | 0.15 |
| 598 | 2.7 | 552 | 0.2 | 521 | 0.3 |
| 597 | 8.0 | 551 | 0.1 | 520 | 0.35 |
| 596 | 0.2 | 550 | 0.15 | 519 | 0.35 |
| | | 549 | 0.2 | 518 | 0.35 |
| 579 and 581: trace, far below 0.1% | | 539 | 0.7 | 507 | 0.3 |
| | | 538 | 2.5 | 506 | 0.7 |
| | | 537 | 2.7 | 505 | 0.7 |
| | | 536 | 6.5 | 504 | 1.4 |
| 570 | 0.3 | 535 | 2.2 | 503 | 0.2 |
| 569 | 1.2 | 534 | 0.3 | 502 | 0.2 |
| 568 | 1.3 | 533 | 0.4 | | |
| 567 | 4.0 | | | 497 | 0.2 |
| 496 | 0.6 | 464 | 0.4 | 422 | 0.2 |
| 495 | 0.4 | 463 | 0.3 | 421 | 0.2 |
| 494 | 1.2 | 462 | 0.4 | 420 | 0.4 |
| 493 | 0.3 | 461 | 0.25 | 419 | 0.2 |
| 492 | 0.2 | | | 418 | 0.25 |
| 491 | 0.15 | 450 | 0.1 | 417 | 0.35 |
| 490 | 0.2 | 449 | 0.15 | | |
| 489 | 0.3 | 448 | 0.2 | 410 | 0.05 |
| 488 | 0.3 | 447 | 0.2 | 409 | 0.1 |
| 487 | 0.2 | 446 | 0.2 | 408 | 0.2 |
| 486 | 0.2 | 445 | 0.3 | 407 | 0.25 |
| | | | | 406 | 0.3 |
| 478 | 0.15 | 441 | 0.1 | 405 | 0.3 |
| 477 | 0.2 | 440 | 0.4 | 404 | 0.2 |
| 476 | 0.25 | 439 | 0.3 | 403 | 0.1 |
| 475 | 0.25 | 438 | 1.1 | 402 | 0.2 |
| 474 | 0.20 | 437 | 0.1 | | |
| 473 | 0.3 | 436 | 0.3 | 380 | 0.1 |

TABLE 2-continued

Lysolipin I
Yellow crystals, $C_{29}H_{24}ClNO_{11}$
Mass spectrum. Di = 140° C.

| m/e | % | m/e | % | m/e | % |
|---|---|---|---|---|---|
|  |  | 435 | 0.2 | 379 | 0.2 |
| 471 | 0.1 | 434 | 0.25 | 378 | 0.3 |
| 470 | 0.1 | 433 | 0.2 | 377 | 0.1 |
| 469 | 0.2 | 432 | 0.1 | from 376–226 |  |
|  |  |  |  | no clear peaks |  |
| 468 | 0.6 | 431 | 0.1 | standing out from |  |
|  |  |  |  | the background, |  |
| 467 | 0.4 | 430 | 0.1 | no peak more |  |
| 466 | 1.5 |  |  | than 0.1% |  |
| 465 | 0.2 | 423 | 0.1 | 225 | 0.2 |
| 224 | 0.2 | 151 | 0.4 | 125 | 0.4 |
| 223 | 0.35 | 150 | 2.7 | 124 | 0.35 |
|  |  | 149 | 3.5 | 123 | 0.6 |
| 219 | 0.2 | 148 | 0.8 | 122 | 0.5 |
| 218 | 0.2 | 147 | 0.6 | 121 | 0.6 |
| 217 | 0.5 | 146 | 0.25 | 120 | 0.4 |
| 216 | 0.2 | 145 | 1.2 | 119 | 0.8 |
| 215 | 0.35 | 144 | 0.3 | 118 | 0.7 |
| 214 | 0.1 | 143 | 0.7 | 117 | 3.9 |
| 213 | 0.3 | 142 | 0.3 | 116 | 0.8 |
| 212 | 0.25 | 141 | 0.6 | 115 | 2.2 |
| 211 | 0.3 | 140 | 0.2 | 114 | 0.3 |
| 210 | 0.5 | 139 | 0.35 | 113 | 0.4 |
|  |  | 138 | 0.3 | 112 | 0.5 |
| 191 | 0.2 | 137 | 0.35 | 111 | 0.4 |
| 190 | 0.3 | 136 | 0.5 | 110 | 0.9 |
| 189 | 0.6 | 135 | 1.2 | 109 | 0.7 |
| 188 | 0.3 | 134 | 0.2 | 108 | 0.4 |
| 187 | 1.0 | 133 | 0.4 | 107 | 1.0 |
| 186 | 0.2 | 132 | 0.6 | 106 | 0.7 |
| 185 | 0.4 | 131 | 4.5 | 105 | 2.5 |
|  |  | 130 | 0.5 | 104 | 0.4 |
| 178 | 0.2 | 129 | 1.6 | 103 | 0.8 |
| 177 | 0.35 | 128 | 1.2 | 102 | 0.4 |
| 176 | 1.0 | 127 | 0.6 | 101 | 0.6 |
| 175 | 0.5 | 126 | 0.3 | 100 | 0.2 |
| 99 | 0.5 | 73 | 2.1 | 45 | 4.8 |
| 98 | 0.8 | 72 | 0.3 | 44 | 3.3 |
| 97 | 1.5 | 71 | 1.7 | 43 | 45 |
| 96 | 0.8 | 70 | 1.6 | 42 | 2.6 |
| 95 | 1.6 | 69 | 3.5 | 41 | 6.1 |
| 94 | 0.6 | 68 | 0.9 | 40 | 0.5 |
| 93 | 1.2 | 67 | 1.4 | 39 | 2.3 |
| 92 | 0.6 | 66 | 0.3 | 38 | 0.6 |
| 91 | 3.4 | 65 | 0.9 | 37 | 0.3 |
| 90 | 0.2 | 64 | 0.3 | 36 | 0.8 |
| 89 | 0.5 | 63 | 0.4 |  |  |
| 88 | 0.2 | 62 | 0.15 | 33 | 2.3 |
| 87 | 0.9 | 61 | 0.5 | 32 | 89 |
| 86 | 0.2 | 60 | 1.8 | 31 | 100 |
| 85 | 1.2 | 59 | 4.8 | 30 | 15 |
| 84 | 1.2 | 58 | 8.5 | 29 | 67 |
| 83 | 3.7 | 57 | 3.2 | 28 | 5.7 |
| 82 | 0.9 | 56 | 1.5 | 27 | 2.6 |
| 81 | 1.5 | 55 | 5.5 | 26 | 0.8 |
| 80 | 0.3 | 54 | 0.5 |  |  |
| 79 | 1.3 | 53 | 1.0 | 19 | 0.7 |
| 78 | 0.7 | 52 | 0.5 | 18 | 6.0 |
| 77 | 1.9 | 51 | 0.8 | 17 | 1.5 |
| 76 | 0.5 | 50 | 1.2 | 16 | 0.3 |
| 75 | 0.6 |  |  | 15 | 26 |
| 74 | 6.3 | 46 | 0.3 | 14 | 2.2 |
|  |  |  |  | reading on the |  |
|  |  |  |  | first trace: 1% = |  |
|  |  |  |  | 27 mm |  |

TABLE 3

Tri-O-acetyl-Lysolipin I
Mass spectrum. Di = 120°

| m/e | I (%) | m/e | I (%) | m/e | I (%) |
|---|---|---|---|---|---|
| 685 | 2 | 607 | 27 | 548 | 2.5 |
| 684 | 8 |  |  | 547 | 1.7 |
| 683 | 24 | 600 metastable ion | | 546 | 3.7 |
| 682 | 21 | 581 metastable ion | |  |  |
| 681 | 58 |  |  | 537 | 2.5 |
|  |  | 581 | 5.5 | 536 | 3.3 |
| 653 | 0.8 | 580 | 15 | 535 | 6.7 |
| 652 | 1.2 | 579 | 17 | 534 | 3.7 |
| 651 | 3.0 | 578 | 40 | 526 | 3.7 |
| 650 | 2.5 | 577 | 7 | 525 | 4.6 |
| 649 | 5.5 | 576 | 2 | 524 | 10.2 |
|  |  |  |  | 523 | 6.2 |
| 643 | 5 | 568 | 1 | 522 | 1.7 |
| 642 | 20 | 567 | 1.3 | 521 | 2.5 |
| 641 | 40 | 566 | 2.5 | 520 | 4.6 |
| 640 | 37 | 565 | 2 | 519 | 5.4 |
| 639 | 100 | 564 | 1.7 | 518 | 7.1 |
|  |  | 563 | 0.9 |  |  |
| 612 | 5 | 562 | 1.3 | 507 | 3 |
| 611 | 16 |  |  | 506 | 4 |
| 610 | 17 | 551 | 1.2 | 505 | 6.2 |
| 609 | 50 | 550 | 1.7 | 504 | 6.7 |
| 608 | 15 | 549 | 4.0 | 503 | 3.3 |
| 502 | 1.6 | 469 | 1.2 | 61 | 2.5 |
|  |  | 468 | 3.3 | 60 | 6.3 |
| 497 | 2.5 | 467 | 1.7 |  |  |
| 496 | 9 | 466 | 4.0 | 57 | 7.5 |
| 495 | 11 | 465 | 3.7 | 56 | 2.5 |
| 494 | 23 | 464 | 5.1 | 55 | 5.4 |
| 493 | 16 | 463 | 6.0 |  |  |
| 492 | 5.4 | 462 | 10 | 45 | 12 |
| 491 | 3.7 | 461 | 8 | 44 | 5 |
| 490 | 3.3 | 460 | 2.5 | 43 | 48 |
| 489 | 3.7 | No significant | | 42 | 13 |
| 488 | 6.3 | peaks from 460 | | 41 | 7 |
| 487 | 4 | to 85 | |  |  |
| 486 | 6 | 85 | 3.3 | 32 | 33 |
|  |  | 84 | 2.0 | 31 | 43 |
| 479 | 1.2 | 83 | 4.4 | 30 | 12 |
| 478 | 3.0 | 82 | 1.7 | 29 | 39 |
| 477 | 3.3 | 81 | 2.0 | 28 | 10 |
| 476 | 3.7 |  |  |  |  |
| 475 | 4.0 | 74 | 12 | 18 | 8 |
| 474 | 2.5 | 73 | 1.7 | 17 | 2 |
| 473 | 2.0 | 72 | 1.2 | 16 | 1.2 |
| 472 | 1.2 | 71 | 5.4 | 15 | 15 |
| 471 | 1.7 | 70 | 3.0 | 14 | 5 |
| 470 | 1.7 | 69 | 9.5 |  |  |

TABLE 4

Lysolipin X
$^{13}C$ NMR spectrum (25.2 MHz). Solvent: $CDCl_3$ + a small amount of DMSO:
The spectrum includes 2 carbonyl signals besides 16 signals of aromatic and 11 signals of aliphatic C-atoms. The signals are characterised in ppm relative to trimethylsilane. Their multiplicity is indicated in parenthesis.

(a) carbonyl peaks
  (1) 175.86 (s)
  (2) 167.86 (s)

(b) signals of C atoms of aromatic character
  (3) 159.11 (s)
  (4) 151.56 (s)
  (5) 149.07 (s)
  (6) 145.1 (s)
  (7) 143.30 (s)
  (8) 140.02 (s)
  (9) 139.2 (s)
  (10) 132.5 (s)
  (11) 126.5 (d)
  (12) 124.1 (s)
  (13) 123.0 (s)
  (14) 120.5 (d)
  (15) 119.2 (s)
  (16) 117.0 (d)
  (17) 115.6 (s)
  (18) 109.9 (s)

(c) signals of C atoms of aliphatic character
  (19) 92.25 (d)
  (20) 90.28 (d)
  (21) 79.02 (d)

TABLE 4-continued (22) 72.7 (d)

(23) 72.35 (s)

(24) 67.3 (d)

(25) 65.03 (d)

(26) 61.83 (q)

(27) 58.37 (q)

(28) 57.54 (q)

(29) 36.21 (q)

TABLE 5

Lysolipin X

IR-spectrum:

(a) absorption bands of a solution in methylene chloride

| 2.71 (w) | 6.37 (m) | 11.31 (m) |
|---|---|---|
| 2.85 (w) | 6.74 (m) | |
| 3.39 (w) | 7.33 (ms) | |
| 6.08 (s) | 8.97 (m) | |
| 6.16 (s) | 9.13 (m) | |
| 6.26 (m) | 9.43 (s) | |

(b) absorption bands of a suspension in nujol

| 2.88 (m) | 6.39 (s) | 9.14 (m) | 11.32 (ms) |
|---|---|---|---|
| 3.02 (m) | 6.97 (s) | 9.56 (s) | 12.79 (ms) |
| 3.67 (w) | 8.00 (s) | 9.80 (m) | |
| 6.12 (ms,shoulder) | 8.57 (m) | 9.98 (s) | |
| 6.21 (s) | 8.91 (m) | 10.23 (m) | |
| 6.28 (s) | 9.00 (m) | 10.61 (m) | |

What we claim is:

1. Lysolipin I of the formula

2. Lysolipin X of the formula

3. A compound which is a member selected from the group consisting of a mono-, a di- and a tri- acylate of Lysolipin I derived from an alkanoic carboxylic acid having from 1 to 7 C atoms.

4. A compound which is a member selected from the group consisting of a mono- a di- and a tri- acylate of Lysolipin X derived from an alkanoic carboxylic acid having from 1 to 7 C atoms.

5. A compound as claimed in claim 3 which is a member selected from the group consisting of the mono-, the di- and the tri- acetate of Lysolipin I.

6. A compound as claimed in claim 4 which is a member selected from the group consisting of the mono-, the di- and the tri-acetate of Lysolipin X.

7. An antibacterial pharmaceutical composition comprising an antibacterially effective amount of Lysolipin I or of one of its acylates derived from an alkanoic carboxylic acid having from 1–7 C-atoms together with a pharmaceutical carrier.

8. An antibacterial pharmaceutical composition comprising an antibacterially effective amount of Lysolipin X or of one of its acylates derived from an alkanoic carboxylic acid having from 1–7 C-atoms together with a pharmaceutical carrier.

* * * * *